(12) United States Patent
Gies et al.

(10) Patent No.: US 11,806,473 B2
(45) Date of Patent: Nov. 7, 2023

(54) VACUUM MONITORING AND MITIGATION SYSTEM

(71) Applicants: Michael P. Gies, Evergreen, CO (US); Roger S. Jussel, Evergreen, CO (US); Charles E. Hellums, Evergreen, CO (US)

(72) Inventors: Michael P. Gies, Evergreen, CO (US); Roger S. Jussel, Evergreen, CO (US); Charles E. Hellums, Evergreen, CO (US)

(*) Notice: Subject to any disclaimer, the term of this patent is extended or adjusted under 35 U.S.C. 154(b) by 825 days.

(21) Appl. No.: 16/799,054

(22) Filed: Feb. 24, 2020

(65) Prior Publication Data
US 2020/0268993 A1 Aug. 27, 2020

Related U.S. Application Data

(60) Provisional application No. 62/810,025, filed on Feb. 25, 2019.

(51) Int. Cl.
| | |
|---|---|
| *A61M 16/20* | (2006.01) |
| *A62C 35/02* | (2006.01) |
| *A62C 37/40* | (2006.01) |
| *A61M 16/00* | (2006.01) |
| *A62C 99/00* | (2010.01) |

(52) U.S. Cl.
CPC ...... *A61M 16/022* (2017.08); *A61M 16/0003* (2014.02); *A61M 16/009* (2013.01); *A61M 16/202* (2014.02); *A62C 35/023* (2013.01); *A62C 37/40* (2013.01); *A62C 99/0018* (2013.01)

(58) Field of Classification Search
CPC ......... A62C 35/023; A62C 37/40; A62C 3/00; A61M 2202/0208; A61M 16/022; A61M 16/0003; A61M 16/202; A61M 16/009
See application file for complete search history.

(56) References Cited

U.S. PATENT DOCUMENTS

2018/0272098 A1* 9/2018 Bottom ................ G05D 11/131

\* cited by examiner

*Primary Examiner* — Christopher R Dandridge
(74) *Attorney, Agent, or Firm* — Leyendecker & Lemire, LLC (57) ABSTRACT

A vacuum monitoring and mitigation system is described. Embodiments of the vacuum monitoring and mitigation system can be implemented in a combined-use vacuum system to help mitigate high oxidizer levels that may damage vacuum pumps of the combined-use vacuum system. The vacuum monitoring and mitigation system can determine when an oxidizer level is above a predetermined threshold and introduce a mitigating gas into the combined-use vacuum system to lower the oxidizer level.

10 Claims, 5 Drawing Sheets

VACUUM MONITORING AND MITIGATION SYSTEM

CROSS-REFERENCE TO RELATED APPLICATION

This application claims the benefit of U.S. Provisional Application No. 62/810,025, filed Feb. 25, 2019.

BACKGROUND

With the introduction of the 2012 edition of NFPA (National Fire Protection Agency) 99 came an entirely new requirement for medical-surgical vacuum systems that are also used for waste anesthetic gas disposal (WAGD). For these combined-use systems, NFPA 99 requires that a total concentration of oxidizers be maintained below 23.6%. NFPA 99 alternatively mandates that the materials, lubricants, and sealants within a vacuum pump must be inert to these oxidizers in lieu of maintaining a concentration of oxidizers below 23.6%.

The perceived hazard that NFPA 99 (2012 edition) addresses is the risk of fire within a vacuum pump system due to the combination of a fuel source (e.g., materials, lubricants, and sealants), an oxidizer, and heat from turbomachinery of the vacuum system. NFPA 99 now requires mitigation of this fire risk either by constructing the source system entirely of inert materials or by maintaining oxidizers within the system below a level of 23.6%. Currently, this requirement only applies to newly installed systems as of July 2016. All systems that have been placed in service prior to this time are currently exempt.

Of significant note, the 2018 edition of NFPA 99 will remove grandfathering for existing installations. As such, all facilities with combined-use vacuum systems will need to meet the previously mentioned requirements once the new rules are adopted by CMS (Centers for Medicare & Medicaid Services).

DETAILED DESCRIPTION

Embodiments of the present invention include a system and a method (or process) for monitoring oxidizer levels in a vacuum system and providing a means of mitigation when oxidizer levels are above a predetermined level. The system can be implemented in a combined-use vacuum system. For instance, combined-use vacuum systems typically found in medical facilities.

In one embodiment, the system can include, but is not limited to, a control module, a mitigating gas supply, a vacuum pressure sensor, an oxidizer sensor, and a valve. The valve can be fluidly connected to the combined-use vacuum system and the mitigating gas supply such that when the valve is opened, a mitigating gas can be introduced into the combined-use vacuum system. Each of the components can be operatively connected to the control module. Since oxygen is a common oxidizer generally found in combined-use vacuum systems, the vacuum monitoring and mitigation system can include an oxygen sensor as the oxidizer sensor. It is to be appreciated that other sensors can be implemented based on the oxidizer being tested for. Embodiments of the present invention can allow for continuous regulation of oxidizer concentration to ensure a concentration of oxidizers in a combined-use vacuum system stays at or below a limit of approximately 23.6% before interacting with pump(s) of the combined-use vacuum system.

In one implementation, the control module can receive input from the oxidizer sensor and the vacuum pressure sensor and determine when the valve needs to be opened based on those inputs. When the valve is opened, an inert gas from the mitigating gas supply can be introduced into a vacuum line of a combined-use vacuum system. The inert gas can be introduced into the vacuum line prior to entering a vacuum pump of the combined-use vacuum system. Generally, the oxidizer sensor can be located upstream of the vacuum pump(s) of the combined-use vacuum system.

In one example embodiment, the control module can be a programmable logic controller (PLC) that interfaces with the oxidizer sensor, the vacuum pressure sensor, and the valve. The valve can be a proportional control valve configured to deliver a mitigating gas (e.g., nitrogen) from the mitigating gas supply to a vacuum line of the combined-use vacuum system. The PLC can monitor oxidizers and vacuum pressure in a vacuum line via the oxidizer sensor and the vacuum pressure sensor. The PLC can be configured to take action based on pre-programmed level thresholds for oxidizer concentration (e.g., oxygen concentrations) and vacuum pressure. Typically, the PLC can be configured to open a valve plumbed to the inert gas source. The PLC can open and close the valve to ensure the level of oxidizers remains below the critical threshold of 23.6%. In one instance, the oxidizer sensor can be a zirconium sensor cell that can operate continuously for 5 or more years and require a minimum of maintenance.

Typically, the system can prioritize vacuum pressure over oxidizer levels. For instance, as long as vacuum pressure remains acceptable, increasing oxidizer levels to the vacuum pump inlet will be mitigated. Stated alternatively, as long as the introduction of the inert gas into the vacuum system does not negatively affect vacuum pressure, the system will mitigate high oxidizer levels when detected.

In a typical implementation, the control module can consistently monitor vacuum pressure in the vacuum line via the vacuum pressure sensor. Based on data collected from the vacuum pressure sensor, the control module can determine if the system is ok to inject the inert gas into the vacuum line if needed. As previously mentioned, the oxygen sensor can be implemented to measure an oxygen concentration of gasses flowing through the vacuum line. When the control module receives data from the oxygen sensor and determines that a concentration of oxidizers is above 23.6%, the control module can send a signal to the valve to open and inject the inert gas into the vacuum line. Based on the oxidizer concentration, the control module can determine how long to keep the valve open for. Of note, if the control module determines that the pressure in the vacuum line has dropped below a predetermined threshold, the control module can close the valve even if data received from the oxygen sensor indicates that the oxidizer concentration is above the predetermined threshold.

The vacuum monitoring and mitigation system can be provided in varying configurations in order to meet the needs of each facility that requires the system. For many in-patient facilities that have very few oxidizer excursions above the NFPA limit of 23.6%, an open loop control approach can be an acceptable and economical option for the facility. Other facilities may experience frequent oxidizer excursions above 23.6% due to smaller system volumes that do not enable dilution of the oxidizers to acceptable levels. In these facilities, a closed loop control approach may be more appropriate because of the varying oxidizer level and duration of each excursion.

In an open loop control, a single oxidizer sensor can be employed. The sensor can be implemented to detect when oxidizer levels in a combined-use vacuum system exceed a control level requiring mitigation. The oxidizer sensor can be located downstream of the mitigating gas supply in order to be able to also confirm the oxidizer levels entering pumps are kept below the NFPA limit. When oxidizer levels require mitigation, the mitigating gas valve can be opened for a pre-determined amount of time to mitigate each expected oxidizer excursion. With an open loop system, the valve open time can be determined by an average high oxidizer excursion time developed from data capture in the facility. The valve can remain open for the average excursion duration time and while vacuum pressure remains above the minimum limit. The vacuum monitoring and mitigation system may close the valve when the timer expires and/or the oxidizer level is below the minimum. The oxidizer level can then be retested and the process can begin again.

In a closed loop control, two oxidizer sensors can be employed. A first oxidizer sensor can be located upstream of the mitigating gas supply to detect when oxidizer levels in the combined-use vacuum system exceed the control level requiring mitigation and when mitigation is no longer required. The second oxidizer sensor can be located downstream of the mitigating gas supply in order to confirm oxidizer levels entering pumps of the combined-use vacuum system are kept below the NFPA limit. As previously mentioned, the upstream oxidizer sensor can provide data to the control module to determine when mitigation may be required and the control module can open the mitigating gas valve until the first oxidizer sensor detects oxidizer levels have dropped below the mitigation control level. The downstream oxidizer sensor can send data to the control module to record oxidizer levels entering the pumps to ensure compliance to the NFPA limit. In the closed loop control, once mitigation begins the valve will remain open until the first oxidizer sensor determines that the oxidizer level has returned to an acceptable level. In one embodiment, built-in hysteresis can be implemented to determine when the oxidizer levels are at an acceptable level.

In high volume nitrous oxide environments (e.g., dental offices and birth centers), the upstream oxidizer sensor can be a nitrous oxide specific sensor. In this embodiment, the upstream oxidizer sensor can detect increasing nitrous oxide percentages and the downstream oxidizer sensor can confirm that oxidizer levels put off by the nitrous oxide have exceeded a warning level in order to mitigate. In the nitrous oxide rich environment, the upstream oxidizer sensor can let the system know when the volume of nitrous oxide has subsided and that the mitigation can subside.

In both the open and closed loop control approaches described above, a 2-position valve can be typically implemented to control mitigating gas flow into the combined-use vacuum system upstream of vacuum pumps. A 2-position on/off valve can be a simple on/off valve implemented to turn on and off a mitigating gas flow. Of note, different valve sizes and orifice sizes can be used to accommodate different flow rates required by each facility system design.

In some facilities, however, a more responsive approach may be required to mitigate oxidizer excursions that vary from slow ramps to fast spikes. At these facilities, the vacuum monitoring and mitigation system can detect oxidizer levels and also an oxidizer rate of change and adjust a flow rate of the mitigating gas into the combined-use vacuum system accordingly. A variable position valve can be implemented to incrementally increase mitigating gas flow proportional to an oxidizer rate of increase. For variable position valves, a rising level of oxidizer that exceeds a high mean operating oxidizer level at the facility can cause the valve to open at a percentage equal to the percentage of oxidizer level above the mean operating oxidizer level. For instance, the amount the variable position valve may open can be determined by the following equation:

$$\text{valve open \%} = ((\text{current oxidizer level} - \text{mean oxidizer level})/\text{mean oxidizer level}) * 100$$

An adjustment parameter can be implemented to allow for a larger valve opening based on the percentage calculation to accommodate for actual site-specific variance. The amount the variable position valve may open can be determined by the following equation:

$$\text{valve open \%} = (((\text{current oxidizer level} - \text{mean oxidizer level})/\text{mean oxidizer level}) * 100) + \text{adjustment \%}$$

The present invention can be embodied as devices, systems, methods, and/or computer program products. Accordingly, the present invention can be embodied in hardware and/or in software (including firmware, resident software, micro-code, etc.). Furthermore, the present invention can take the form of a computer program product on a computer-usable or computer-readable storage medium having computer-usable or computer-readable program code embodied in the medium for use by or in connection with an instruction execution system. In one embodiment, the present invention can be embodied as non-transitory computer-readable media. In the context of this document, a computer-usable or computer-readable medium can include, but is not limited to, any medium that can contain, store, communicate, propagate, or transport the program for use by or in connection with the instruction execution system, apparatus, or device.

The computer-usable or computer-readable medium can be, but is not limited to, an electronic, magnetic, optical, electromagnetic, infrared, or semiconductor system, apparatus, device, or propagation medium.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

The term "software," as used in this specification and the appended claims, refers to programs, procedures, rules, instructions, and any associated documentation pertaining to the operation of a system.

The term "firmware," as used in this specification and the appended claims, refers to computer programs, procedures, rules, instructions, and any associated documentation contained permanently in a hardware device and can also be flashware.

The term "hardware," as used in this specification and the appended claims, refers to the physical, electrical, and mechanical parts of a system.

The terms "computer-usable medium" or "computer-readable medium," as used in this specification and the appended claims, refers to any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

The term "signal," as used in this specification and the appended claims, refers to a signal that has one or more of its characteristics set or changed in such a manner as to encode information in the signal. It is to be appreciated that wireless means of sending signals can be implemented including, but not limited to, Bluetooth, Wi-Fi, acoustic, RF, infrared and other wireless means.

The term "oxidizer," as used in this specification and the appended claims, refers generally to an oxidizing agent. Oxidizing agents can include, but are not limited to, oxygen, ozone, hydrogen peroxide, nitrous oxide, hypochlorite, etc.

A First Embodiment of a Vacuum Monitoring and Mitigation System

Figure 1:
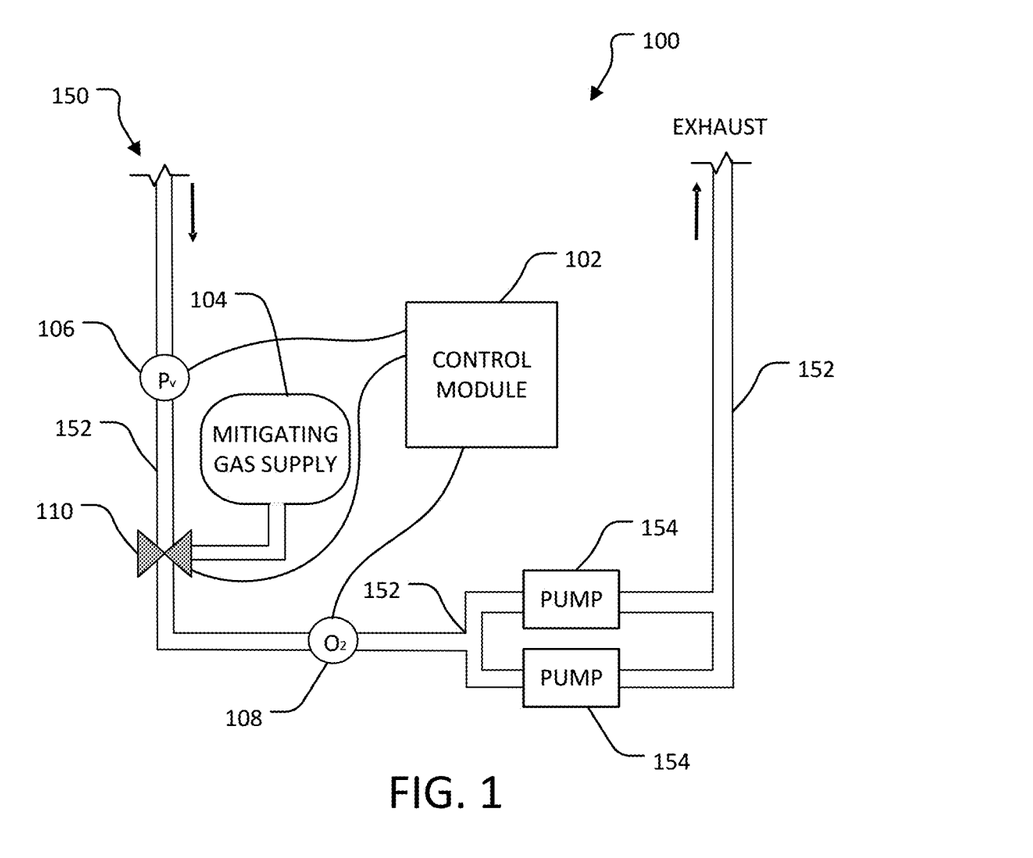
FIG. 1 is a detailed diagram of a vacuum monitoring and mitigation system according to one embodiment of the present invention.

Referring to FIG. 1, a block diagram of a first embodiment 100 of a vacuum monitoring and mitigation system is illustrated. The vacuum monitoring and mitigation system 100 can typically be implemented in a combined-use vacuum system 150. For instance, combined-use vacuum systems can typically be found in medical facilities. The vacuum monitoring and mitigation system 100 can be used to detect high concentrations of oxidizers and mitigate (or lower) the concentration of the oxidizers by introducing an inert (or substantially inert) gas into the combined-use vacuum system 150. The combined-use vacuum system 150 can include a pipe assembly 152 and one or more vacuum pumps 154.

The vacuum monitoring and mitigation system 100 can include, but is not limited to, a control module 102, a mitigating gas supply 104, a vacuum pressure sensor 106, an oxidizer sensor 108, and a valve 110. The vacuum pressure sensor 106 and the oxidizer sensor 108 can be adapted to send data to the control module 102. The valve 110 can be operatively connected to the control module 102 such that the control module 102 can send a signal to the valve 110 to open and close. The mitigating gas supply 104 can be fluidly connected to the combined-use vacuum system 150 via the valve 110. Typically, the components of the VMMS system 100 can be installed and/or retrofitted to an existing combined-use vacuum system.

In one embodiment, the oxidizer sensor 108 can be an oxygen sensor adapted to determine an amount of oxygen in the combined-use vacuum system 150. Based on the amount of oxygen, the control module 102 can determine an oxidizer percentage in the combined-used vacuum system 150. The oxidizer levels can be implemented to determine when to open the valve 110 and introduce a mitigating gas to the combined-use vacuum system 150. As can be appreciated, by introducing the mitigating gas, the oxidizer levels can be effectively lowered thus lowering a chance of an issue in the one or more vacuum pumps 154.

As shown, the vacuum pressure sensor 106 can be located upstream of the valve 110 and the oxygen sensor 108 can be located downstream of the valve 110. Typically, the oxygen sensor 108 can be located upstream of a manifold where the vacuum line splits to different pumps 154 of the combined-use vacuum system 150. By monitoring the oxidizer level prior to the vacuum pumps 154 of the combined-use vacuum system 150, the VMMS 100 can help ensure that the oxidizer levels do no exceed the threshold before entering the vacuum pumps 154.

Figure 2:
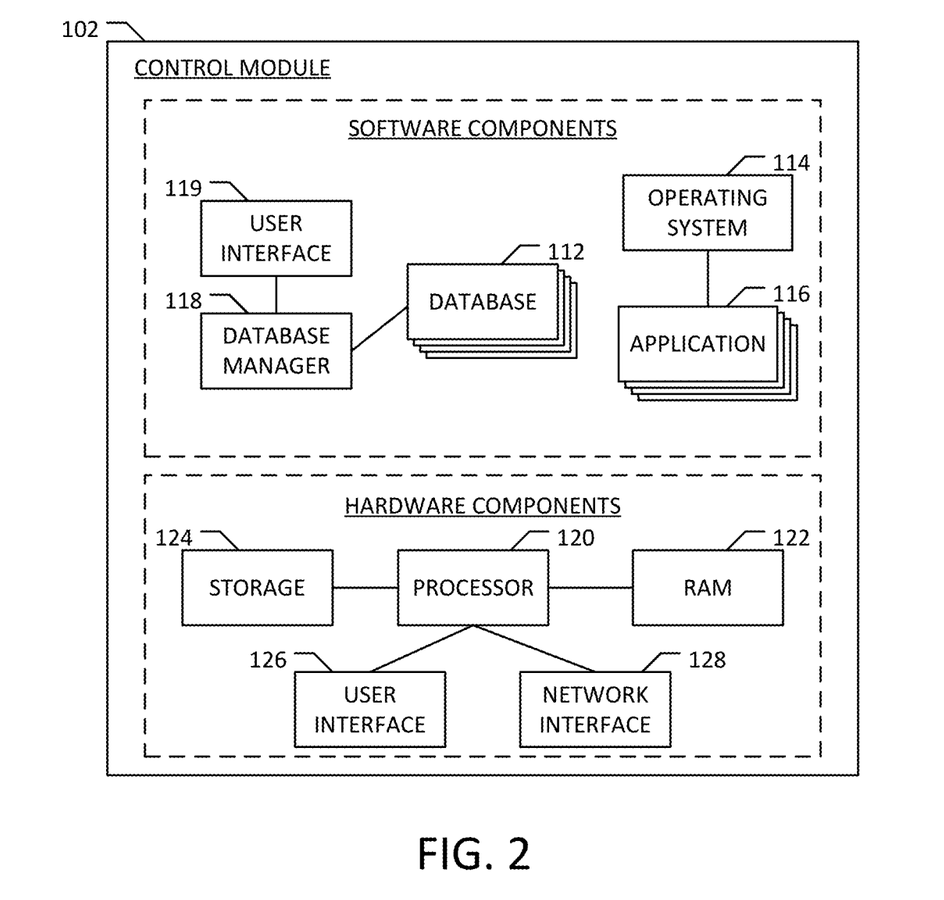
FIG. 2 is a block diagram of a control module according to one embodiment of the present invention.

Referring to FIG. 2, a block diagram of one embodiment of the control module 102 is illustrated.

Generally, data related to pressure, oxidizer percentages, mitigating gasses, times for keeping the valve 110 open, etc. can be stored in the control module 102. For instance, the data can be stored in one or more databases 112 of the control module 102. In some instances, the data can be stored in databases remotely located from one another. It is to be appreciated that the data may be stored externally to the control module 102. For instance, the databases 112 can be remotely located from the control module 102.

The control module 102 can represent a server or another powerful, dedicated computer system that can support multiple user sessions. In some embodiments, the control module 102 can be any type of computing device including, but not limited to, a personal computer, a game console, a smartphone, a tablet, a netbook computer, or other computing devices. In one embodiment, the control module 102 can be a distributed system wherein server functions are distributed over several computers connected to a network. The control module 102 can typically include a hardware platform and software components.

The software components of the control module 102 can include the one or more databases 112 which can store combined-use vacuum system 150 information and data. The software components can also include an operating system 114 on which various applications (or programs) 116 can execute. A database manager 118 can be an application that runs queries against the databases 112. In one embodiment, the database manager 118 can allow interaction with the databases 112 through an HTML user interface on a remotely located device. In another instance, a user can have direct access to the databases 112. For example, the control module 102 can include a user interface (or web-based interface) 319 to access the databases 112.

The hardware platform of the control module 102 can include, but is not limited to, a processor 120, random access memory 122, and nonvolatile storage 124. The processor 120 can be a single microprocessor, multi-core processor, or a group of processors. The random access memory 122 can store executable code as well as data that can be immediately accessible to the processor 120. The nonvolatile storage 124 can store executable code and data in a persistent state.

The hardware platform can include a user interface 126. The user interface 126 can include keyboards, monitors, pointing devices, and other user interface components. The hardware platform can also include a network interface 128. The network interface 128 can include, but is not limited to, hardwired and wireless interfaces through which the control module 102 can communicate with other devices. In some instances, the control module 102 can communicate with the vacuum pressure sensor 106, the oxygen sensor 108, and the valve 110 via the network interface 128. In other instances, the control module 102 can communicate with the vacuum pressure sensor 106, the oxygen sensor 108, and the valve 110 via hardwired connections and the user interface 126. In yet other instances, a combination of wireless and wired connections can be implemented to operatively connect the control module 102 to the vacuum pressure sensor 106, the oxygen sensor 108, and the valve 110. In some embodiments, more than one control module can be implemented.

Figure 3:
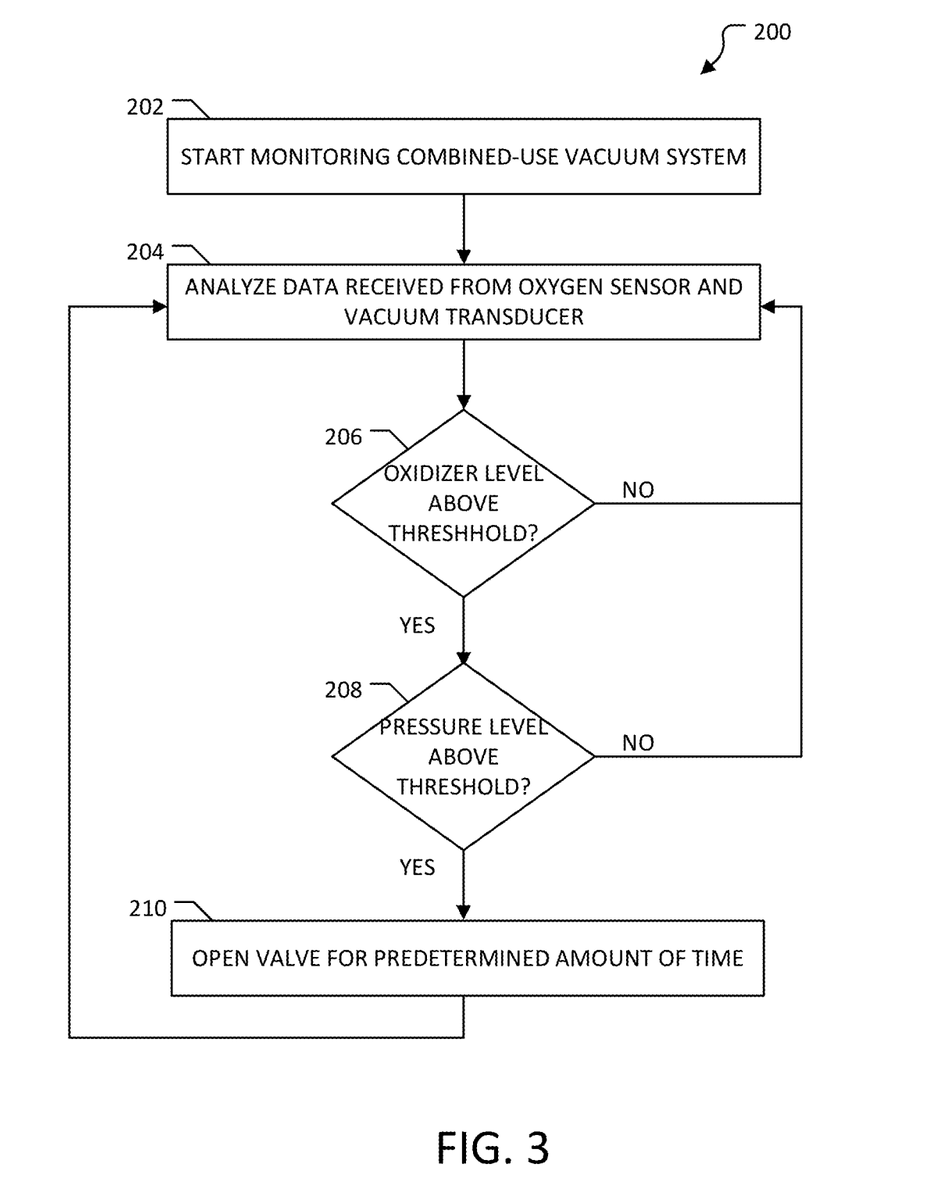
FIG. 3 is a flow chart of a method of implementing a vacuum monitoring and mitigation system according to one embodiment of the present invention.

Referring to FIG. 3, a flow diagram of one example method (or process) 200 of implementing the vacuum monitoring and mitigation system 100 is illustrated. Typically, the process 200 can be implemented after a combined-use vacuum system 150 has been modified with components of the vacuum monitoring and mitigation system 100. In some instances, a combined-use vacuum system 150 can be initially installed in a hospital or similar medical building with the vacuum monitoring and mitigation system 100.

In block 202, the control module 102 can start to monitor a combined-use vacuum system. Monitoring the combined-use vacuum system can typically include the control module 102 receiving data or information from the vacuum pressure sensor 106 and the oxygen sensor 108.

In block 204, the control module 102 can continuously analyze the data received from the vacuum pressure sensor 106 and the oxygen sensor 108. Analyzing the data can include, but is not limited to, determining an oxidizer level based on data received from the oxygen sensor 108 and determining a pressure level based on data received from the vacuum pressure sensor 106.

After analyzing the data in block 204, the process 200 can move to decision block 206. In decision block 206, the control module 102 can determine if the oxidizer level is above a predetermined threshold. If the oxidizer level is not above the predetermined threshold, the process 200 can move back to block 204. Typically, the control module 102 can analyze new data from the oxygen sensor 108 and the vacuum pressure sensor 106 after determining that the oxidizer level is below the predetermined threshold. Of note, although the control module 102 may be continuously receiving data from the oxygen sensor 108, the control module 102 can be adapted to only analyze data every $n^{th}$ time receiving the data. For instance, the control module 102 may only analyze the data every 5 seconds.

If the oxidizer level is above the predetermined threshold, the process 200 can move to decision block 208. In decision block 208, the control module 102 can determine if the pressure level in the combined-use vacuum system 150 is above a predetermined threshold. If the pressure level is below the predetermined threshold, the process 200 can move back to block 204. If the pressure level is above the predetermined threshold, the process 200 can move to block 210. In some embodiments, the control module 102 may continuously analyze data received from the vacuum transducer 106 to ensure that the pressure is above the predetermined threshold. If the control module 102 determines the pressure in the vacuum line of the combined-use vacuum system 150 is below the threshold, the control module 102 may send a signal to the valve 110 to close if open. As can be appreciated, the vacuum monitoring and mitigation system 100 may prioritize ensuring sufficient pressure in the vacuum line over negating oxidizer levels.

In block 210, the control module 102 can send a signal to the valve 110 to open. When the valve 110 is opened, the mitigating gas can be introduced into the combined-use vacuum system 150. In one instance, the control module 102 can send another signal to the valve 110 to close after a predetermined amount of time based on the oxidizer level. In another instance, the control module 102 can send a signal to close the valve 110 based on determining that the oxidizer level has lowered below the threshold level. In yet another instance, the valve 110 can open for a predetermined amount of time based on receiving the signal to open from the control module 102 and can close automatically after the predetermined amount of time has lapsed. As previously mentioned, the control module 102 may continue to receive and analyze data from the vacuum transducer 106. If the control module 102 determines that a pressure in the vacuum line of the combined-use vacuum system 150 has dropped below the predetermined threshold, the control module 102 can send a signal to the valve 110 to close.

After the mitigating gas has been introduced into the combined-use vacuum system 150, the process 200 can move back to block 204 and continuously monitor the combined-use vacuum system 150.

A Second Embodiment of a Vacuum Monitoring and Mitigation System

Figure 4:
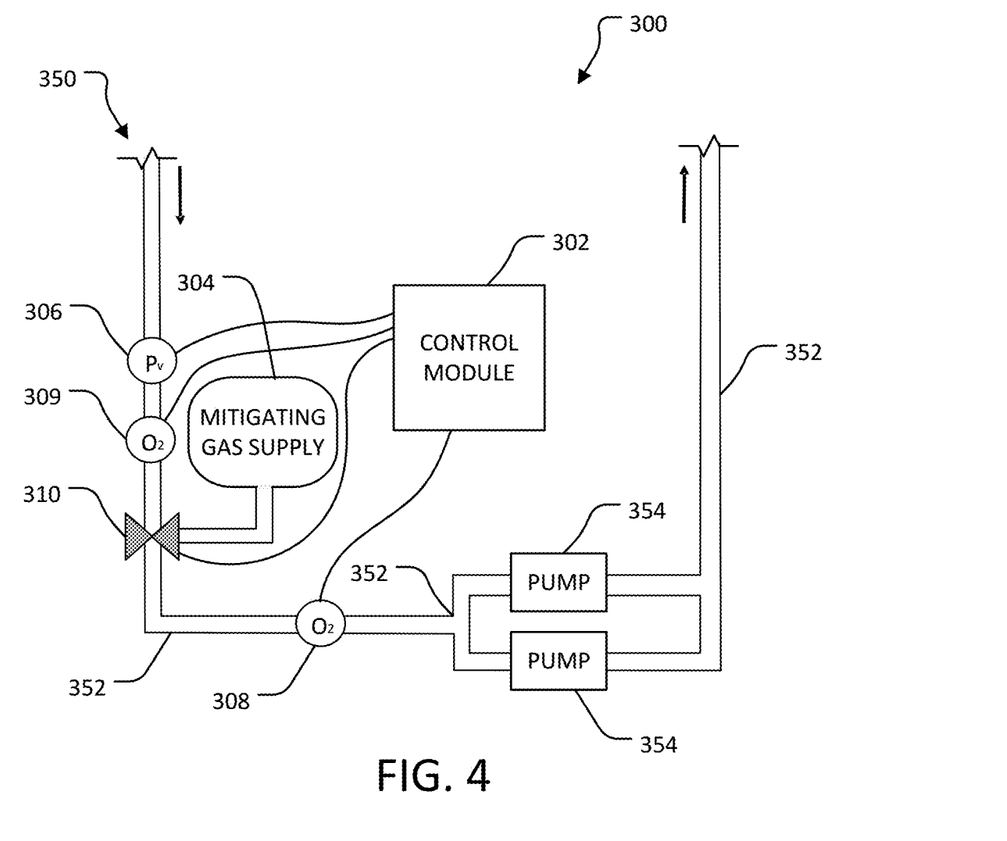
FIG. 4 is a detailed diagram of a vacuum monitoring and mitigation system according to one embodiment of the present invention.

Referring to FIG. 4, a block diagram of a second embodiment 300 of a vacuum monitoring and mitigation system is illustrated. The second embodiment vacuum monitoring and mitigation system 300 can typically be implemented in a combined-use vacuum system 350. For instance, combined-use vacuum systems can typically be found in medical facilities. The second embodiment vacuum monitoring and mitigation system 300 can be used to detect high concentrations of oxidizers and mitigate (or lower) the concentration of the oxidizers by introducing an inert (or substantially inert) gas into the combined-use vacuum system 350.

The vacuum monitoring and mitigation system 300 can include, but is not limited to, a control module 302, a mitigating gas supply 304, a vacuum pressure sensor 306, a first oxidizer sensor 308, a second oxidizer sensor 309, and a valve 310. The vacuum pressure sensor 306, the first oxidizer sensor 308, and the second oxidizer sensor 309 can be adapted to send data to the control module 302. The valve 310 can be operatively connected to the control module 302 such that the control module 302 can send a signal to the valve 310 to open and close. The mitigating gas supply 304 can be fluidly connected to the combined-use vacuum system 350 via the valve 310.

The control module 302 can be substantially similar to the first embodiment control module 102. In one embodiment, the first oxidizer sensor 308 and the second oxidizer sensor 309 can both be oxygen sensors. In another embodiment, the first oxidizer sensor 308 can be an oxygen sensor and the second oxidizer sensor 309 can be a nitrous oxide sensor. Typically, a nitrous oxide sensor can be implemented in high-volume nitrous oxide environments (e.g., dental office, birth center, etc.).

As shown, the vacuum pressure sensor 306 and the second oxidizer sensor 309 can each be located upstream of the valve 310. The first oxidizer sensor 308 can be located downstream of the valve 310. Typically, the first oxidizer sensor 308 can be located upstream of a manifold where the vacuum line 352 splits to different pumps 354 of the combined-use vacuum system 350.

Figure 5:
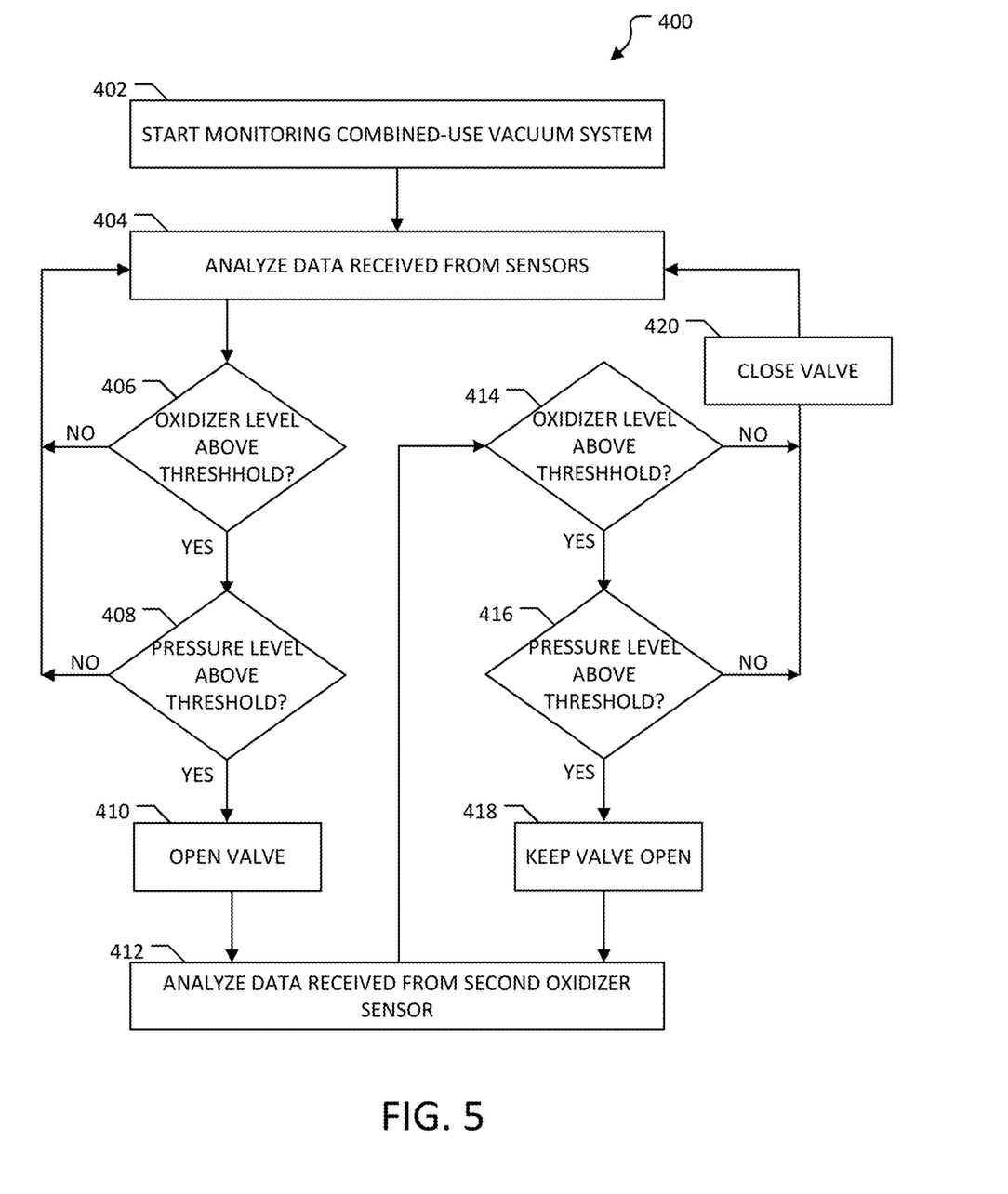
FIG. 5 is a flow chart of a method of implementing a vacuum monitoring and mitigation system according to one embodiment of the present invention.

Referring to FIG. 5, a flow diagram of one example method (or process) 400 of implementing the vacuum monitoring and mitigation system 300 is illustrated. Typically, the process 400 can be implemented after a combined-use vacuum system 350 has been modified with components of the second embodiment vacuum monitoring and mitigation system 300. In some instances, the combined-use vacuum system 350 can be initially installed in a hospital or similar medical building with the second embodiment vacuum monitoring and mitigation system 300.

In block 402, the control module 302 can start to monitor a combined-use vacuum system. Monitoring the combined-use vacuum system can typically include the control module 302 receiving data or information from the vacuum pressure sensor 306 and the oxygen sensor 308.

In block 404, the control module 302 can continuously analyze the data received from the vacuum pressure sensor 306, the first oxidizer sensor 308, and the second oxidizer sensor 309. Analyzing the data can include, but is not limited to, determining an oxidizer level based on data received from the first oxidizer sensor 308 and the second oxidizer sensor 309 and determining a pressure level based on data received from the vacuum pressure sensor 306.

After analyzing the data in block 404, the process 400 can move to decision block 406. In decision block 406, the control module 302 can determine if the oxidizer level is above a predetermined threshold. Typically, data from the second oxidizer sensor 309 can be used to make a determination. If the oxidizer level is not above the predetermined threshold, the process 400 can move back to block 404.

Typically, the control module 302 can analyze new data from the first oxidizer sensor 308, the second oxidizer sensor 309, and the vacuum pressure sensor 306 after determining that the oxidizer level is below the predetermined threshold. Of note, although the control module 302 may be continuously receiving data from the oxidizer sensors 308-309, the control module 302 can be adapted to only analyze data every $n^{th}$ time receiving the data. For instance, the control module 302 may only analyze new data every 5 seconds.

If the oxidizer level is above the predetermined threshold, the process 400 can move to decision block 408. In decision block 408, the control module 302 can determine if the pressure level in the combined-use vacuum system 350 is above a predetermined threshold. If the pressure level is below the predetermined threshold, the process 400 can move back to block 404. If the pressure level is above the predetermined threshold, the process 400 can move to block 410.

In block 410, the control module 302 can send a signal to the valve 310 to open. When the valve is opened, the mitigating gas can be introduced into the combined-use vacuum system 350. After the valve 310 has been opened, the process 400 can move to block 412.

In block 412, the control module 302 can analyze data received from the vacuum pressure sensor 306, the first oxidizer sensor 308, and the second oxidizer sensor 309. Analyzing the data can include, but is not limited to, determining an oxidizer level based on data received from the first oxidizer sensor 308 and the second oxidizer sensor 309 and determining a pressure level based on data received from the vacuum pressure sensor 306.

After analyzing the data in block 412, the process 400 can move to decision block 414. In decision block 414, the control module 302 can determine if the oxidizer level is above the predetermined threshold. Typically, data from the second oxidizer sensor 309 can be used to make a determination. If the oxidizer level is not above the predetermined threshold, the process 400 can move back to block 420.

If the oxidizer level is above the predetermined threshold, the process 400 can move to decision block 416. In decision block 416, the control module 302 can determine if the pressure level in the combined-use vacuum system 350 is above a predetermined threshold. If the pressure level is below the predetermined threshold, the process 400 can move back to block 420. If the pressure level is above the predetermined threshold, the process 400 can move to block 418.

In block 418, the valve 310 can be kept open to allow the mitigating gas to be introduced into the combined-use vacuum system 350. The process 400 can then move back to block 412 to analyze data from the sensors 306, 308, 309 with the valve 310 open and the mitigating gas continuously being introduced to the system 350.

When either the oxidizer level is determined to be below the predetermined threshold or the pressure in the system 350 is below the pressure threshold, the control module 302 can send a signal to the valve 310 to close in block 420. After the valve 310 has been closed, the process 400 can move back to block 404 to analyze data from the sensors 306, 308, 309 with the valve 310 closed.

ALTERNATIVE EMBODIMENTS AND VARIATIONS

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

We claim:

1. A method of implementing a vacuum monitoring and mitigation system, the method comprising:
   providing the vacuum monitoring and mitigation system, the system including:
   a control module;
   a vacuum pressure sensor adapted to measure pressure;
   an oxygen sensor adapted to measure a concentration of oxygen;
   a mitigating gas supply; and
   a valve (i) fluidly connected to the mitigating gas supply and (ii) operatively connected to the control module;
   by the control module, monitoring a combined-use vacuum system, the valve being fluidly connected to the combined-use vacuum system; and
   by the control module, introducing a mitigating gas into the combined-use vacuum system from the mitigating gas supply based on determining an oxidizer level in the combined-use vacuum system is above a predetermined threshold;
   wherein the combined-use vacuum system is defined by a pipe assembly fluidly connected to one or more pumps in a medical facility.

2. The method of claim 1, wherein the step of monitoring includes:
   receiving data from the oxygen sensor;
   determining if an oxidizer level is above a predetermined threshold, the oxidizer level being based on an oxygen concentration in the combined-use vacuum system;
   receiving data from the vacuum pressure sensor; and
   determining if a pressure level in the combined-use vacuum system is above a predetermined pressure threshold.

3. The method of claim 2, wherein the mitigating gas is only introduced when (i) the oxidizer level is above the predetermined threshold and (ii) a pressure in the combined-use vacuum system is above the predetermined pressure threshold.

4. The method of claim 2, wherein the step of determining if the oxidizer level is above the predetermined threshold includes:
   analyzing the data received from the oxygen sensor;
   determining the oxidizer level based on the analyzed data; and
   determining if the oxidizer level is above the predetermined threshold.

5. The method of claim 1, wherein the oxygen sensor and the vacuum pressure sensor are located within a vacuum line of the combined-use vacuum system.

6. The method of claim 5, wherein the vacuum pressure sensor is located upstream of the oxygen sensor and the valve.

7. The method of claim 6, wherein the oxygen sensor is located upstream of a vacuum pump of the combined-use vacuum system and downstream of the valve.

8. The method of claim 1, wherein the control module sends a signal to the valve to open when determining that the oxidizer level is above the predetermined threshold.

9. The method of claim 1, wherein the mitigating gas supply is filled with an inert gas.

10. A method of implementing a vacuum monitoring and mitigation system in a combined-use vacuum system in a medical facility, the method comprising:
    by a control module, receiving data from a vacuum pressure sensor located upstream of a vacuum pump manifold in a vacuum line of the combined-use vacuum system;
    by the control module, receiving data from an oxygen sensor located downstream of the vacuum pressure sensor in the vacuum line;
    by a control module, analyzing data received from the oxygen sensor and the vacuum pressure sensor;
    by a control module, determining (i) an oxidizer level based on the data received from the oxygen sensor and (ii) if the oxidizer level is above a predetermined threshold;
    by a control module, determining if a pressure level in the combined-use vacuum system is above a predetermined pressure threshold based on the data received from the vacuum pressure sensor; and
    by a control module, introducing a mitigating gas when (i) the oxidizer level is above the predetermined threshold and (ii) the pressure level in the combined-use vacuum system is above the predetermined pressure threshold;
    wherein (i) a mitigating gas supply storing the mitigating gas is fluidly connected to the combined-use vacuum system via a valve operatively connected to the control module; and (ii) the combined-use vacuum system is defined by a pipe assembly fluidly connected to one or more pumps in the medical facility.

* * * * *